US008012750B2

(12) United States Patent
Har-Noy

(10) Patent No.: US 8,012,750 B2
(45) Date of Patent: *Sep. 6, 2011

(54) T-CELL ACTIVATION DEVICE

(75) Inventor: Michael Har-Noy, Modi'in (IL)

(73) Assignee: Immunovative Therapies Ltd., Shoham (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/533,668

(22) Filed: Jul. 31, 2009

(65) Prior Publication Data

US 2009/0291498 A1 Nov. 26, 2009

Related U.S. Application Data

(60) Division of application No. 11/601,446, filed on Nov. 17, 2006, now Pat. No. 7,592,431, which is a continuation-in-part of application No. 11/066,133, filed on Feb. 24, 2005, now Pat. No. 7,678,572.

(60) Provisional application No. 60/547,966, filed on Feb. 26, 2004.

(51) Int. Cl.
C12N 5/00 (2006.01)
C12N 5/02 (2006.01)

(52) U.S. Cl. ...................... 435/372.3; 435/377

(58) Field of Classification Search .................. None
See application file for complete search history.

(56) References Cited

U.S. PATENT DOCUMENTS

| 4,279,249 | A | 7/1981 | Vert et al. |
| 5,126,132 | A | 6/1992 | Rosenberg |
| 5,443,983 | A | 8/1995 | Ochoa et al. |
| 5,766,920 | A | 6/1998 | Babbitt et al. |
| 5,806,529 | A | 9/1998 | Reisner et al. |
| 5,846,827 | A | 12/1998 | Celis et al. |
| 6,040,177 | A | 3/2000 | Riddell et al. |
| 6,194,207 | B1 | 2/2001 | Bell et al. |
| 6,251,385 | B1 | 6/2001 | Terman |
| 6,255,073 | B1 | 7/2001 | Cai et al. |
| 6,352,694 | B1 | 3/2002 | June et al. |
| 6,500,193 | B1 | 12/2002 | Bezemer et al. |
| 6,511,511 | B1 | 1/2003 | Slivka et al. |
| 6,514,286 | B1 | 2/2003 | Leatherbury et al. |
| 6,534,055 | B1 | 3/2003 | June et al. |
| 6,572,894 | B2 | 6/2003 | Rossling et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,402,431 | B2 | 7/2008 | Har-Noy |
| 7,435,592 | B2 | 10/2008 | Har-Noy |
| 7,592,431 | B2 | 9/2009 | Har-Noy |
| 7,678,572 | B2 * | 3/2010 | Har-Noy ............... 435/372.3 |
| 2002/0127208 | A1 | 9/2002 | Waller et al. |
| 2003/0004578 | A1 | 1/2003 | Brown et al. |
| 2003/0175272 | A1 | 9/2003 | Gruenberg |
| 2003/0215946 | A1 | 11/2003 | Nair et al. |
| 2005/0065593 | A1 | 3/2005 | Chu et al. |
| 2005/0191291 | A1 | 9/2005 | Har-Noy |
| 2005/0191746 | A1 | 9/2005 | Van et al. |
| 2006/0036331 | A1 | 2/2006 | Lu et al. |
| 2006/0121021 | A1 | 6/2006 | Hunig |

FOREIGN PATENT DOCUMENTS

| EP | 0319012 A2 | 6/1989 |
| WO | 94012196 | 6/1994 |
| WO | WO04012196 | 6/1994 |
| WO | 97046256 A1 | 12/1997 |
| WO | 99024045 A1 | 5/1999 |
| WO | 01062895 A2 | 8/2001 |
| WO | WO03038062 A1 | 10/2002 |
| WO | 03024989 A2 | 3/2003 |
| WO | 2004004768 A1 | 1/2004 |
| WO | 2005001074 A | 1/2005 |
| WO | 2005081982 A | 9/2005 |
| WO | 2005084276 A | 9/2005 |

OTHER PUBLICATIONS

Meier et al: "Development of a Latex Conjugated Immuno Cytological Marker for Scanning Electron Microscopic Analysis of Quail Chick Chimeras", Journal of Experimental Zoology, vol. 224, No. 1, 1982, pp. 25-38.
Dinauer et al: "Selective Targeting of Antibody-Conjugated Nanoparticles to Leukemic Cells and Primary T-Lymphocytes", Biomaterials, vol. 26, No. 29, Oct. 2005, pp. 5898-5906.
Sinha et al.: "Biodegradable Microspheres for Protein Delivery", Journal of Controlled Release, vol. 90, No. 3, Jul. 31, 2003, pp. 261-280.
Supplementary European Search Report, Jan. 20, 2010.
Antn, J. H. et al (1992). "Cyokine Dysegulaton and Acue GaftVersus-Hot Dsease." Blood, vol. 80, No. 12: pp. 2964-2968.
Andeson, P. et al. (1988) "Cossinkng CD3 wth CD2 Using Sephaose-Immobiized Antbodies Enhances T Lymphocyte Proliferation." Cellular Immunology, vol. 115, No. 2: pp. 246-256.
Asselin-Paturel et al. (1998). "Quantitative Analysis of Th1, Th2 and TGF-β1 Cytokine Expression in Tumor, TIL and PBL of Non-Small Cell Lung Cancer Patients." Int. J. Cancer, vol. 77, No. 1: pp. 7-12.

(Continued)

Primary Examiner — Michail Belyavskyi
(74) Attorney, Agent, or Firm — Westman, Champlin & Kelly, P.A.; Z. Peter Sawicki

(57) ABSTRACT

A biodegradable device for activating T-cells includes a biodegradable support and a binder attached to the biodegradable support, the binder having reactivity to one or more agents capable of binding to a T-cell surface antigen.

9 Claims, No Drawings

OTHER PUBLICATIONS

Bachmann, M. F. et al. (1997). "Distinct Roles for LFA-1 and CD28 During Activation of Naive T Cells: Adhesion Versus Costimulation." Immunity, vol. 7, No. 4: pp. 549-557.

Banu, N. et al. (1999). "Tgf-β1 down-regulates induced expression of both class II MHC and B7-1 on primary murine renal tubular epithelial cells." Kidney International, vol. 56, No. 3: pp. 985-994. 0.

Baroja, M.L. et al. (1989). "The Anti-T Cell Monoclonal Antibody 9.3 (Anti-CD28) Provides a Helper Signal and Bypasses the Need for Accessory Cells in T Cell Activation with Immobilized Anti-CD3 and Mitogens." Cellular Immunology, vol. 120, No. 1: pp. 205-217.

Baxevans, C. N. et al. (2000. "Compomised ant-umor esponses in tumor necrss factor-α knockout mice." Eur J. Immuno)., vol. 30, No. 7: pp. 1957-1966.

Belardelli, F. et al. (2002). "Cytokines as a link between innate and adaptive antitumor immunity." Trends in Immunology, vol. 23 No. 4: pp. 201-208.

Blazar, B. R. et al. (1997). "Recent advances in graft-versus-host disease (GVHD) prevention." Immunological Reviews, vol. 157: pp. 79-109.

Blazar, B. R. et al. (1998). "Rapamycin Inhibits the Generation of Graft-Versus-Host Disease- and Graft-VersusLeukemia-Causing T Cells by Interfering with the Production of Th1 or Th1 Cytotoxic Cytokines." Journal of Immunology, vol. 160, No. 11: pp. 5355-5365.

Carayol, G. et al. (1997). "Quantitative Analysis of T Helper 1, T Helper 2, and Inflammatory Cytokine Expression in Patients After Allogeneic Bone Narrow Transplantation: Relationship with the Occurrence of Acute Graft-Versus-Host Disease." Transplantation, vol. 63, No. 9: pp. 1307-1313.

Carpenter A. F., G. Auf et al. (2003). "CpG-olgonuceotdes for cancer immunoherapy : review of the literature and potential applications in malignant glioma." Front Biosci 8: E115-27.

Chambers, C. A et l. (1999) "Costmulaoy regulaton of T cell functon." Curent Opinion in Cell Biology, vol. 11, No. 2: pp. 203-210.

Champlin, R., I. Khouri, et al. (1999). "Allogeneic hematopoietic transplantation as adoptive immunotherapy. Induction of graft-versus-malignancy as primary therapy." Hematol Oncol Clin North Am 13(5): 1041-57, vii-viii.

Champlin, R., K. van Besien, et al. (2000). "Allogeneic hematopoietic transplantation for chronic lymphocytic leukemia and lymphoma: potential for nonablative preparative regimens." Curr Oncol Rep 2(2): 182-91.

Chang, J. W., M. Peng, et al. (2000). "Induction of Th1 response by dendritic cells pulsed with autologous melanoma apoptotic bodies." Anticancer Res 20(3A): 1329-36.

Chen, Q. et al. (1994). "Production of IL-10 by Melanoma Cells: Examination of its Role in Immunosuppression Mediated by Melanoma." Int. J. Cancer, vol. 56, No. 5: pp. 755-760.

Childs, R. et al. (200). "Nonmyeoablatve Sem Cell Transplanation for Soid Tumors: Expanding the Application of Allogeneic Immunotherapy." Seminars in Hematology, vol. 39, No. 1: pp. 63-71.

Childs, R. et al. (2000). "Regression of metastatic renal-cell carcinoma after nonmyeloablative allogeneic peripheral-blood stem-cell transplantation." The New England Journal of Medicine, vol. 343, No. 11: pp. 750-758.

Childs, R. W. (2000). "Nonmyeloablative allogeneic peripheral blood stem-cell transplantation as immunotherapy for malignant diseases." Cancer J 6(3): 179-87.

Childs, R. W. (2002). "Immunotherapy of solid tumors: nonmyeloablative allogeneic stem cell transplantation." MedGenMed 4(3): 13.

Cerc, M. et al. (1993). "A TH1—>TH2 swtch is a crtcal sep in the etology of HIV infection." Immunology Today, vol. 14, No. 3: pp. 107-111.

Cohen, P. A., L. P ng, et al. 2000 ). "CD4+ T cells in adoptive immunotherapy and the indirect mechanism of tumor rejection." Crit. Rev. Immunol 20(1):17-56.

Damle, N. K et al (1989). "Stmulaton Via the CD3 and CD28 Moecules Induces Responsveness to IL-4 in CD4 +CD29+CD45R-Memory T Lymphocytes." The Journal of Immunology, vol. 143, No. 6: pp. 1761-1767.

Das, H. S. Imoto, et al. (2001). "Kinetc anaysis of cyokne gene expression in patens wth GVHD after donor lymphocyte infusion." Bone Marrow Transplant 27(4): 373-80.

Daubener, W. et al. (1995). "Establishment of T-helper type 1- and T-helper type 2-like human Toxoplasma antigen-specific T-cell clones." Immunology, vol. 86, No. 1: pp. 79-84.

Deeths, M. J. et al (1999) "CD8+ T Cells Become Nonresponsve (Anergic) Folowing Activation in the Presence of Costimulation." The Journal of Immunology, vol. 163, No. 1: pp. 102-110.

De Vita, F., M. Orditura, et al. (2000). "Serum interleukin-10 is an independent prognostic factor in advanced solid tumors." Oncol Rep 7(2): 357-61.

de Waal Malefyt, R. et al. (1993). "Direct Effects of IL-10 on Subsets of Human CD4+ T Cell Clones and Resting T Cells. Specific Inhibition of IL-2 Production and Proliferation." The Journal of Immunology, vol. 150, No. 11: pp. 4754-4765.

D'Orazio, T. J. et al. (1998). "A Novel Role for TGFf-β and IL-10 in the Induction of Immune Privilege." The Journal of Immunology, vol. 160, No. 5: 2089-2098.

Dudley, M. E. et al. (2002). "Cancer Regression and Autoimmunity in Patients After Clonal Repopulation with Antitumor Lymphocytes." Science, vol. 298, No. 5594: pp. 850-854.

Egeter, O. et al. (2000). "Eradication of Disseminated Lymphomas with CpG-DNA Activated T Helper Type 1 Cells from Nontransgenic Mice." Cancer Research, vol. 60, No. 6: 1515-1520.

Eibl, B. et al. (1996). "Evidence for a Graft-Versus-Tumor Effect in a Patient Treated With Marrow Ablative Chemotherapy and Allogeneic Bone Marrow Transplantation for Breast Cancer." Blood, vol. 88, No. 4: pp. 1501-1508.

Esasse-Beile, U. et al (1999). "Semiquantitative analysis of Th1 and Th2 cyokne expession in CD3+, CD4+, and CD8+ renal-cell-carcinoma-infiltrating lymphocytes." Cancer Immunol Immunother, vol. 48, No. 4: pp. 204-208.

Emori, Y., H. Sasaki, et al. (1996). "Effect of Z-100, an immunomodulator extracted from human type tubercle bacilli, on the pulmonary metastases of Lewis lung carcinoma in attempt to regulate suppressor T cells and suppressor factor, IL-4." Biotherapy 9(4): 249-56.

Ertl, B., F. Heigl, et al. (2000). "Lectin-mediated bioadhesion: preparation, stability and caco-2 binding of wheat germ agglutinin-functionalized Poly(D,L-lactic-co-glycolic acid)-microspheres." J Drug Targt 8(3): 173-84.

Fan, X. G., W. E. Liu, et al. (1998). "Circulating Th1 and Th2 cytokines in patients with hepatitis C virus infection." Mediators Inflamm 7(4): 295-7.

Finke, J. H., P. Rayman, et a. (1992). "Chaacerzaton of a human renal cel carcnoma specfc cyooxic CD8+T cell line." J Immunother 11(1): 1-11.

Finke, J. H., P. Rayman, et al. (1994). "Characterization of tumor-infiltrating lymphocyte subsets from human renal cell carcinoma: specific reactivity defined by cytotoxicity, interferon-gamma secretion, and proliferation." J Immunother Emphasis Tumor Immunol 15(2): 91-104.

Flanagan, D. L. et al. (1999). "Th1 Cytokines and NK Cells Participate in the Development of Murine Syngeneic Graft- Versus-Host Disease." The Journal of Immunology, vol. 163, No. 3: pp. 1170-1177.

Fowler, D. H., J. Breglio, et al. (1996). "Allospecific CD4+, Th1/Th2 and CD8+, Tc1/Tc2 populations in murine GVL: type I cells generate GVL and type 11 cells abrogate GVL." Biol Blood Marrow Transplant 2(3): 118-25.

Fowler, D. H. and R. E. Gress (2000). "Th2 and Tc2 cells in the regulation of GVHD, GVL, and graft rejection: considerations for the allogeneic transplantation therapy of leukemia and )ymphoma." Leuk Lymphoma 38(3-4): 221-34.

Frassoni, F., M. Labopin, et al. (1996). "Results of allogeneic bone marrow transplantation for acute leukemia have improved in Europe with time—a report of the acute leukemia working party of the European group for blood and marrow transplantation (EBMT)." Bone Marrow Transplant 17(1): 13-8.

Freeman, G. J. et al. (2002). "Protect the killer: CTLs need defenses against the tumor." Nature Medicine, vol. 8, No. 8: pp. 787-789.

Friess, H., H. G. Beger, et al. (1996). "Treatment of advanced pancreatic cancer with mistletoe: results of a pilot trial." Anticancer Res 16(2): 915-20.

Fujimoto, T. et al. (1997). "Streptococcal Preparation OK-432 is a Potent Inducer of IL-12 and a T Helper Cell 1 Dominant State." The Journal of Immunology, vol. 158, No. 12: pp. 5619-5626.

Fujisao, S. et al. (1998). "Th1/Th2 balance alteration in the clinical course of a patient with pure red cell aplasia and thymoma." British Journal of Haematology, vol. 103, No. 2: pp. 308-310.

Gabrilovich, D. I. et al. (1996). "Dendritic Cells in Antitumor Immune Responses. II. Dendritic Cells Grown from Bone Marrow Precursors, but Not Mature Dc from Tumor-Bearing Mice, Are Effective Antigen Carriers in the Therapy of Established Tumors." Cellular Immunology, vol. 170, No. 1: pp. 111-119.

Gale, R. P. et al. (1984). "How Does Bone-Marrow Transplantation Cure Leukaemia?" The Lancet, vol. 2, No. 8393: pp. 28-30.

Garlie, N. K., A.V. LeFever, et al. (1999). "T cells coactivated with immobilized anti-CD3 and anti-CD28 as potential immunotherapy for cancer." J Immunother 22(4): 336-45.

Geppert, T.D. et al. (1988). "Activation of T Lymphocytes by Immobilized Monoclonal Antibodies to CD3, Regulatory Influences of Monoclonal Antibodies to Additional T Cell Surface Determinants." J. Clin. Invest., vol. 81: pp. 1497-1505.

Ghosh, P., K. L. Komschlies, et al. (1995). "Gradual loss of T-helper 1 populations in spleen of mice during progressive tumor growth." J Natl Cancer Inst 87(19): 1478-83.

Gorelik, L., A. Prokhorova, et al. (1994). "Low-dose melphalan-induced shift in the production of a Th2-type cytokine to a Th1-type cytokine in mice bearing a large MOPC-315 tumor." Cancer Immunol Immunother 39(2): 117-26.

Grakoui, A. et al. (1999). "The Immunological Synapse: A Molecular Machine Controlling T Cell Activation." Science, vol. 285, No. 5425: pp. 221-227.

Granucci, F. et al. (2001). "Transcriptional reprogramming of dendritic cells by differentiation stimuli." Eur J Immunol, vol. 31, No. 9: pp. 2539-2546.

Grigg, A., P. Bardy, et al. (1999). "Fludarabine-based non-myeloablative chemotherapy followed by infusion of HLA-identical stem cells for relapsed leukaemia and lymphoma." Bone Marrow Transplant 23(2): 107-10.

Grohmann, U., M. C. Moretti, et al. (1998). "Dendritic cells, interleukin 12, and CD4+ lymphocytes in the initiation of class I-restricted reactivity to a tumor/self peptide." Crit Rev Immunol 18(1-2): 87-98.

Hara, I., H. Hotta, et al. (1996). "Rejection of mouse renal cell carcinoma elicited by local secretion of interleukin-2." Jpn J Cancer Res 87(7): 724-9.

Heine, G. et al. (2002). "A shift in the Th(1)/Th(2) ratio accompanies the clinical remission of systemic lupus erythematosus in patients with end-stage renal disease." Nephrology Dialysis Transplantion, vol. 17, No. 10: pp. 1790-1794.

Heniford, B. T. et al. (1994). "Interleukin-8 Suppresses the Toxicity and Antitumor Effect of Interleukin-2." Journal of Surgical Research, vol. 56, No. 1: pp. 82-8.

Herlyn, D. and B. Birebent (1999). "Advances in cancer vaccine development." Ann Med 31(1): 66-78.

Horiguchi, S. et al. (1999). "Primary Chemically Induced Tumors Induce Profound Immunosuppression Concomitant with Apoptosis and Alterations in Signal Transduction in T Cells and NK Cells." Cancer Research, vol. 59, No. 12: pp. 2950-2956.

Inagawa, H., T. Nishizawa, et al. (1998). "Mechanisms by which chemotherapeutic agents augment the antitumor effects of tumor necrosis factor: involvement of the pattern shift of cytokines from Th2 to Th1 in tumor lesions." Anticancer Res 18(5D): 3957-64.

Ito, N. et al. (1999). "Lung Carcinoma: Analysis of T Helper Type 1 and 2 Cells and T Cytotoxic Type 1 and 2 Cells by Intracellular Cytokine Detection with Flow Cytometry." Cancer, vol. 85, No. 11: pp. 2359-2367.

Janes, P. W. et al. (1999). "Aggregation of Lipid Rafts Accompanies Signaling Via the T Cell Antigen Receptor." the Journal of Cell Biology, vol. 147, No. 2: pp. 447-461.

Jung, U. et al. (Nov. 2003). "CD3/CD28-costimulated T1 and T2 subsets: differential in vivo allosensitization generates distinct GVT and GVHD effects." Blood, vol. 1, No. 9: pp. 3439-3446.

Kadowaki, N. et al. (2002). "Natural Type I Interferon-Producing Cells as a Link Between Innate and Adaptive Immunity." Human Immunology, vol. 63, No. 12: pp. 1126-1132.

Kai, S. and H. Hare (2003). "Allogeneic hematopoietic stem cell transplantation." Therap Apher Dial 7(3): 285-91.

Kasakura, S. (1998) "[A role for T-helper type 1 and type 2 cytokines in the pahogeness of various human diseases]" Rinsho Byori 46(9): 915-21.

Kitahara, S., M. Ikeda, et al. (1996). "Inhibition of head and neck metastatic and/or recurrent cancer by local administration of multicytokine inducer Ok-432." J Laryngol Otol 110(5): 449-53.

Knoefel, B., K. Nuske, et al. (1997). "Renal cell carcinomas produce IL-6, IL-10, IL-11, and TGF-beta 1 in primary cultures and modulate T lymphocyte blast transformation." J Interferon Cytokine Res 17(2): 95-102.

Kobayashi, M . et al ( 1998 ). "A Pathogenic Role of Th2 Cells and Their Cytokine Products on the Pulmonary Metasasis ofMurine B16 Meanoma."The Journal of Immunology, vol. 160, No. 12: pp. 5869-5873.

Kobayashi, M., R. B. Pollard, et al. (1997). "Inhibition of pulmonary metastasis by Z-100, an immunomodulatory lipid-arabinomannan extracted from *Mycobacterium tuberculosis*, in mice inoculated with B16 melanoma." Anticancer Drugs 8(2): 156-63.

Lahn, M. et al. (1999). "PRo-Infammaory and T Cell Inhibtory Cytokines Are Seceed at Hgh Levels in Tumor Cell Cultures of Human Renal Cell Carcinoma." European Urology, vol. 35, No. 1: pp. 70-80.

Langenkamp, A. et al. (2000). "Kinetics of dendritic cell activation: impact on priming of TH1, TH2 and nonpolarized T cells." Nature Immunology, vol. 1, No. 4: 311-316.

Laux, I. et al. (2000). "Response Differences between Human CD4(+) and CD8(+) T-Cells during CD28 Costimulation: Implications for Immune Cell-Based Therapies and Studies Related to the Expansion of Double-Positive T-Cells during Aging." Clinical Immunology, vol. 96, No. 3: pp. 187-197.

Le Bon, A. et al. (2002) "Links between innate and adaptve immunity via type I intefreon." Current Opinion Immunology, vol. 14, No. 4: pp. 432-436.

Lee, P. P. et al. (1997). "T Helper 2-Dominant Antilymphoma Immune Response Is Associated With Fatal Outcome." Blood, vol. 90, No. 4: pp. 1611-1617.

Levine, B.L. et al. (1997). "Effects of CD28 Costimulation on Long-Term Proliferation of CD4+ T Cells in the Absence of Exogenous Feeder Cells." the Journal of Immunology, vol. 159, No. 12: pp. 5921-5930.

Li, L. et al. (1998). "Cyclophosphamide Given After Active Specific Immunization Augments Antitumor Immunity by Modulation of Th1 Commitment of CD4+T Cells." Journal of Surgical Oncology, vol. 67, No. 4: pp. 221-227.

Liebowitz, D. N. et al. (1998). "Costimulatory approaches to adoptive immunotherapy." Current Opinion Oncology, vol. 10, No. 6: pp. 533-541.

Lowes, M. A. G. A. Bshop, et al. (1997) "T helper 1 cyokine mRNA is inceased in spotnaneously regressing primary melanomas." J Invest Dermatol 108(6): 914-9.

Ludviksson, B. R. et al. (2000). "The effect of TGF-β1 on immune responses of naive versus memory CD4+ Th1/Th2 T cells." Eur J Immunol, vol. 30, No. 7: pp. 2101-11.

Lum, L.G. et al (2001) "Immune moduaton in cancer patens after adoptve tansfer of an-CD3/anti-CD28-costimulated T-cells—phase I clinical trial." Journal of Immunotherapy, vol. 24, No. 5: pp. 408-419.

Ma, J. et al (1998). "Use of encapsuaed single chain antibodies for induction of an-idioypic humoral and cellular immune responses." Journal of Pharmaceutical Sciences, Vo. 87, No. 11: pp. 1375-1378.

Maeurer, M. J., D. M. Martin, et al. (1995). "Host immune response in renal cell cancer: interleukin-4 (IL-4) and IL-10 mRNA are frequently detected in freshly collected tumor-infiltrating lymphocytes." Cancer Immunol Immunother 41(2): 111-21.

Maus, M. V et al (2002). "Ex vvo expansion of polyconal and antgen-specific cyooxic T lymphocyes by artfcial APCs expressing ligands for the T-cell receptor, CD28 and 4-1BB." Nature Biotechnology, vol. 20, No. 2: pp. 143-148.

Menetrier-Caux, C. et al. (1999). "Renal cell carcinoma induces interleukin 10 and prostaglandin E2 production by monocytes." British Journal of Cancer, vol. 79, No. 1: pp. 119-130.

Moran, M. et al. (1998). "Engagement of GPI-Linked CD48 Contributes to TCR Signals and Cytoskeletal Reorganization: A Role for Lipid Rafts in T Cell Activation." Immunity, vol. 9, No. 6: pp. 787-796.

Muller, M. et al. (2003). "Surface modification of PLGA microspheres." Journal of Biomedic Material Research, vol. 66A,No. 1: pp. 55-61.

Naboulin, R. et al (199). "Inereukn-10 is a poent inhibtor of tumor cyooxicty by human monocyes and aveolar macrophages." Journal of Leukocyte Biology, vol. 55, No. 4: pp. 437-442.

Nakagomi, H. et al. (1995). "Lack of Interleukin-2 (IL-2) Expression and Selective Expression of IL-10 mRNA in Human Renal Cell Carcinoma." Int Journal of Cancer, vol. 63, No. 3: pp. 366-371.

Nishimua, T. et al. (2000. "The critical role of Th1-dominant immunity in tumor immunology." Cancer Chemother Pharmacol, vol. 46 (Suppl): S52-S61.

Nta, T, M. Hshii, et al. (1994). "Selectve expession of interleukin-10 gene wthin globasoma multiforme." Brain Res 649(1-2): 122-8.

O'Donnel P.B. et al (1997). "Preparation of microspheres by the solvent evaporation technique." Advanced Drug Delivery Reviews, vol. 28, No. 1: pp. 25-42.

Oka, H. et al. (1999). "An immunomodulatory arabinomannan extracted from *Mycobacterium tuberculosis*, Z-100, restores the balance of Th1/Th2 cell responses in tumor bearing mice." Immunology Letters, vol. 70, No. 2: pp. 109-117.

Okamoto, T. et al. (1997). "Local Injection of OK432 Can Augment the TH1-Type T-Cell Response in Tumor-Draining Lymph Node Cells and Increase Their Immunotherapeutical Potential." International Journal of Cancer, vol. 70, No. 5: pp. 598-605.

Okutomi, T., Y. Kato, et al. (200 0). "[Clinical effecs of aduvant th erap y u sing Z-100 (Ancer 20 injecton) for oral cancer—prevention o fstomatitis and hematopoietic impairment]. " Gan To Kagaku Ryoho 27(1):65-71.

Onishi T. et al (1999). "An assessment of the immunological environment based on intratumoral cytokine production in renal cell carcinoma." BJU International, vol. 83, No. 4: pp. 488-492.

Raghupathy, R. (1997). "Th1-type immunity is incompatible with successful pregnancy." Immunology Today, vol. 18, No. 10: pp. 478-82 0.

Raghupath y, R . et al (1999) . "Matenal Th1- and Th2-Type Reactivity to Placental Antgens in Normal Human Pregnancy and Unexplained Recurrent Spontaneous Abortons."Ce lular Immunology, vol. 196, No. 2: pp. 122-130.

Rondon, G., S. Giralt, et al. (1996). "Graft-versus-leukemia effect after allogeneic bone marrow transplantation for chronic lymphocytic leukemia." Bone Marrow Transplant 18(3): 669-72.

Rosenbeg, S. A. (2001). "Progress in the development of immunotherapy for the treatment of patients with cancer" Journal of Internal Medicine, vol. 250, No. 6: pp. 462-475.

Roussel, E. et al. (1996). "Predominance of a type 2 intratumoural immune response in fresh tumour-infiltrating lymphocytes from human gliomas." Clinical and Experimental Immunology, vol. 105, No. 2: pp. 344-352.

Rubbi, C.P. et al. (1993). "Evidence of surface antigen detachment during incubation of cells with immunomagnetic beads." Journal of Immunology Methods, vol. 166, No. 2: pp. 233-241.

Santin, A. D. et al. (2000). "Interleukin-10 Increases Th1 Cytokine Production and Cytotoxic Potential in Human Papillomavirus-Specific CD8(+) Cytotoxic T Lymphocytes." Journal of Virology, vol. 74, No. 10: pp. 4729-4737.

Sao, M ., S. Goo, et al (1998 ). "Impaired production of Th1 cyokines and increased frequency of Th2 subsets in PBMC from advanced cancer patients." 18(5D): 3951-5.

Saxton, M. L. et al. (1997). "Adoptive Transfer of Anti-CD3-Activated CD4+ T Cells Plus Cyclophosphamide and Liposome-Encapsulated Interleukin-2 Cure Murine Mc-38 and 3LL Tumors and Establish Tumor-Specific Immunity." Blood, vol. 89, No. 7: pp. 2529-2536.

Shibuya, T.Y. et al. 2000. "Anti-CD3/Ant-CD28 Bead Stmulaton Overomes CD3 Unesponsveness in Patients With Head and Neck Squamous Cell Carcinoma." Arch Otolaryngol Head Neck Surg, vol. 126, No. 4: 473-479.

Shinomiya, Y., M. Harada, et al. (1995). "Anti-metastatic activity induced by the in vivo activation of purified protein derivative (PPD)-recognizing Th1 type CD4+ T cells." Immunobiology 193(5): 439-55.

Shurin, M. R., L. Lu, et al. (1999). "Th1/Th2 balance in cancer, transplantation and pregnancy." Springer Semin lmmunopathol 21(3): 339-59.

Slavin, S. et al. (2001). "Non-myeloablative allogeneic Stem cell transplantation focusing on immunotherapy of life-threatening malignant and non-malignant diseases." Critical Reviews Oncology Hematology, vol. 39, No. 1-2: pp. 25-29.

Slavin, S. et al. (1995). "Allogeneic cell therapy for relapsed leukemia after bone marrow transplantation with donor peripheral blood lymphocytes." Experimental Hematology, vol. 23, No. 14: pp. 1553-1562.

Slavin, S. et al. (1996). "Allogeneic Cell Therapy With Donor Peripheral Blood Cells and Recombinant Human Interleukin-2 to Treat Leukemia Relapse After Allogeneic Bone Marrow Transplantation." Blood, vol. 87, No. 6: pp. 2195-1204.

Slavin, S. et al. (1996). "Allogeneic Cell Therapy: The Treatment of Choice for All Hematologic Malignancies Relapsing Post Bmt." Blood, vol. 87, No. 9: pp. 4011-4013.

Slavin, S. et al. (2001). "Nonmyeloablative stem cell transplantation for the treatment of cancer and life-threatening nonmalignant disorders: past accomplishments and future goals." Cancer Chemother Pharmacol, vol. 48, (Suppl 1): pp. S79-S84.

Slavin, S. et al. (1998). "Immunotherapy in conjunction with autologous and allogeneic blood or marrow transplantation in lymphoma." Annals of Oncology, vol. 9 (Suppl 1): pp. S31-S39.

Smith, D. R., S. L. Kunkel, et al. (1994). "Production of interleukin-10 by human bronchogenic carcinoma." Am J Pathol 145(1): 18-25.

Smyth, M. J. et al. (2002). "New Aspects of Natural-Killer-Cell Surveillance and Therapy of Cancer." Nature Reviews Cancer, vol. 2, No. 11: pp. 850-861.

Sredni, B. et al. (1995). "Bone Marrow-Sparing and Prevention of Alopecia by AS101 in Non-Small-Cell Lung Cancer Patients Treated with Carboplatin and Etoposide." Journal of Clinical Oncology, vol. 13, No. 9: pp. 2342-2353.

Sedni B tal (1996)"Pedominane of TH1 Response in Tumor Bearing Mice and CancerPatients Treated with AS101." National Journal of Cancer Institute, vol. 88, No. 18: pp. 1276-1284.

Sredni, B., R. H. Xu, et al. (1996). "The protective role of the immunomodulator AS101 against chemotherapy-induced alopecia studies on human and animal models." Int J Cancer 65(1): 97-103.

Sein, G., W Henn , et al. (199 8). "Modulation of the cellular and humoral immune reponses of tumor patients by mistletoe therapy." Eur J Med Res 3(4): 194-202.

Stern, B. V. et al. (2002). "Vaccination with Tumor Peptide in CpG Adjuvant Protects Via IFN-Gamma-Dependent CD4 Cell Immunity." The Journal of Immunology, vol. 168, No. 12: pp. 6099-6105.

Tabata, T. et al. (1999). "Th2 Subset Dominance Among Peripheral Blood T Lymphocytes in Patients with Digestive Cancers." American Journal of Surgery, vol. 177, No. 3: pp. 203-208.

Taga, K. et al. (1993). "Human Interleukin-10 Can Directly Inhibit T-Cell Growth." Blood, vol. 81, No. 11: pp. 2964-2971.

Takeuchi T etal (1 997) "Th2-like response and antitumor effect of anti-interleukin-4 mAb in mice bearing renal cell carcinoma." Cancer Immunol Immunother, vol. 43, No. 6: pp. 375-381.

Tanaka, K., K. Kemmotsu, et al. (1998). "[Flow cytometric analysis of helper T cell subsets (Th1 and Th2) in healthy adults]." Rinsho Byori 46(12): 1247-51.

Tanaka, J., M. lmamura, et al. (1997). "The important balance between cytokines derived from type 1 and type 2 helper T cells in the control of graft-versus-host disease." Bone Marrow Transplant 19(6): 571-6.

Tatsumi, T. et al. (2002). "Disease-associated bias in T helper type 1 (Th1)/Th2 CD4(+) T cell responses against Mage-6 in HLA-DRB10401(+) patients with renal cell carcinoma or melanoma." Journal of Experimental Medicine, vol. 196, No. 5: pp. 619-628.

Terao, H., M. Harada, et al. (1994). "Th1 type CD4+T cells may be a potent effector against poorly immunogenic syngeneic tumors." Biotherapy 8(2): 143-51.

Tessmar J. et al. (2003). "The use of poly(ethylene glycol-block-poly(lactic acid) derived copolymers for the rapid creation of biomimetic surfaces." Biomaterials. vol. 24, No. 24: pp. 4475-4486.

Thanhauser, A., A. Bohle, et al. (1995). "The induction of bacillus-Calmette-Guerin-activated killer cells requires the presence of monocytes and T-helper type-1 cells." Cancer Immunol Immunother 40(2): 103-8.

Thomas, A. K. et al. (2002). "A Cell-Based Artificial Antigen-Presenting Cell Coated with Anti-CD3 and CD28 Antibodies Enables Rapid Expansion and Long-Term Growth of CD4 T Lymphocytes." Clinical Immunology, vol. 105, No. 3: pp. 259-272.

Thomas, E., R. Storb, et al. (1975). "Bone-marrow transplantation (first of two parts)." N Engl J Med 292(16): 832-43.

Thomas, E. D., R. Storb, et al. (1975). "Bone-marrow transplantation (second of two parts)." N Engl J Med 292(17): 895-902.

Tilg, H. et al. (1994). "Interleukin-6 (IL-6) as an Anti-inflammatory Cytokine: Induction of Circulating IL-1 Receptor Antagonist and Soluble Tumor Necrosis Factor Receptor p55." Blood, vol. 83, No. 1: pp. 113-118.

To, W. C. et al. (2000). "Therapeutic Efficacy of Th1 and Th2 L-selectin—CD4+ Tumor-Reactive T Cells." Laryngoscope vol. 110, (10 Pt 1): pp. 1648-1654.

Ueno, N. T., G. Rondon, et al. (1998). "Allogeneic peripheral-blood progenitor-cell transplantation for poor-risk patients with metastatic breast cancer." J Clin Oncol 16(3): 986-93.

van Besien, K., P. Thall, et al. (1997). "Allogeneic transplantation for recurrent or refractory non-Hodgkin's lymphoma with poor prognostic features after conditioning with thiotepa, busulfan, and cyclophosphamide: experience in 44 consecutive patients." Biol Blood Marrow Transplant 3(3): 150-6. 0.

Voutsadakis, I. A. (2003). "Nk cells in allogeneic bone marrow transplantation." Cancer Immunol lmmunother, vol. 52, No. 9: pp, 525-534.

Vowels, B. R. et al. (1994). "Th2 Cytokine mRNA Expression in Skin in Cutaneous T-Cell Lymphoma." The Journal of Investigative Dermatology, vol. 103, No. 5: pp. 669-673.

Wang, Q et al (1995) "Selective Cytokine Gene Expression in Renal Cell Carcinoma Tumor Cells and Tumor-Infiltrating Lymphocytes." International Journal of Cancer, vol. 61, No. 6: pp. 780-785.

Weber, K., U. Mengs, et al (1998). "Effects of a sandardized mitleoe prepaaton on metasatc B16 melanoma colonization in murine lungs." Arzneimittelforschung 48(5): 497-502.

Weiden, P. L et al (1981). "Antileukemic Effect of Chronic Graft-Versus-Host Disease: Contribution to Impoved Survival After Allogeneic Marrow Transplantation." New England Journal of Medicine, vol. 304, No. 25: pp. 1529-1533.

Whitmore, M. et al. (1999). "LPD lipopolyplex initiates a potent cytokine response and inhibits tumor growth." Gene Therapy, vol. 6, No. 11: pp. 1867-1875.

Wong, B. R. et al. (1999). "Trance is a TNF family member that regulates dendritic cell and osteoclast function." Journal of Leukocyte Biology, vol. 65, No. 6: pp. 715-724.

Woo, E. Y. et al. (2001). "Regulatory CD4(+)CD25(+) T Cells in Tumors from Patients with Early-Stage Non-Small Cell Lung Cancer and Late-Stage Ovarian Cancer." Cancer Research, vol. 61, No. 12: pp. 4766-4772.

Woo, E. Y. et al. (2002). "Cutting edge: Regulatory T Cells from Lung Cancer Patients Directly Inhibit Autologous T cell proliferation." J Immunol 168(9): 4272-6.

Yamamura, M. (1992). "Defining protective responses to pathogens: cytokine profiles in leprosy lesions." Science 255 (5040): 12.

Yashiro-Ohtani, Y. et al. (2000). "Non-CD28 Costimulatory Molecules Present in T Cell Rafts Induce T Cell Costimulation by Enhancing the Association of TCR with Rafts." the Journal of Immunology, vol. 164, No. 3: pp. 1251-1259.

Yoon, T. J. et al. (1998). "Prophylactic effect of Korean mistletoe (Viscum album coloratum) extract on tumor metastasis is mediated by enhancement of NK cell activity." International Journal of Immunopharmacology, Vo. 20, No. 4-5: pp. 163-172.

Zitvogel, L. et al. (1996). "Therapy of Murine Tumors with Tumor Peptide-Pulsed Dendritic Cells: Dependence on T Cells, B7 Costimulation, and T Helper Cell 1-associated Cytokines." Journal of Experimentive Medicine, vol. 183, No. 1: pp. 87-97.

Agrewala et al., "Delivery of antigen in allogeneic cells preferentially generates CD4+ Th1 cells", Clinical and Experimental Immunology, 2003, vol. 134, pp. 13-22.

* cited by examiner

T-CELL ACTIVATION DEVICE

CROSS-REFERENCE TO RELATED APPLICATION

The present application is a divisional of and claims priority of U.S. patent application Ser. No. 11/601,446, filed Nov. 17, 2006, now U.S. Pat. No. 7,592,431, which is a continuation-in-part of Ser. No. 11/066,133, filed Feb. 24, 2005, now U.S. Pat. No. 7,678,572, the content of which is hereby incorporated by reference in its entirety; and the present application also claims priority of U.S. Provisional Application No. 60/547,966, filed Feb. 26, 2004, the content of which is hereby incorporated by reference in its entirety.

FIELD OF INVENTION

This invention relates to a biodegradable device for activating, expanding and differentiating T-cells for use in cell therapy treatment protocols.

BACKGROUND

Cell therapy methods have been developed in order to enhance the host immune response to tumors, viruses and bacterial pathogens. Cell therapy methods often involve the ex-vivo activation and expansion of T-cells. Examples of these type of treatments include the use of tumor infiltrating lymphocyte (TIL) cells (see U.S. Pat. No. 5,126,132 issued to Rosenberg), cytotoxic T-cells (see U.S. Pat. No. 6,255,073 issued to Cai, et al.; and U.S. Pat. No. 5,846,827 issued to Celis, et al.), expanded tumor draining lymph node cells (see U.S. Pat. No. 6,251,385 issued to Terman), and various other lymphocyte preparations (see U.S. Pat. No. 6,194,207 issued to Bell, et al.; U.S. Pat. No. 5,443,983 issued to Ochoa, et al.; U.S. Pat. No. 6,040,177 issued to Riddell, et al.; U.S. Pat. No. 5,766,920 issued to Babbitt, et al.).

T-cells must be activated in order to proliferate, perform effector functions and produce cytokines (Liebowitz, Lee et al. 1998). T-cells require direct contact with antigen presenting cells ("APC") for activation. APC convert protein antigens to peptides and then present peptide-MHC complexes in a form that can be recognized by T-cells. The interaction of the peptide-MHC complex on the APC and the T-cell receptor ("TCR") on the surface of the T-cell usually provides the first of the two signals required for activation. The second of the two signals required for activation is usually provided by membrane-bound or secreted products of the APC.

Due to the difficulty in maintaining large numbers of natural APC in cultures and in identifying disease-associated antigens and controlling the processing and presentation of these antigens to T-cells by natural APC, alternative methods have been sought for ex-vivo activation of T-cells for use in cell therapy. One method is to by-pass the need for the peptide-MHC complex on natural APC by instead stimulating the TCR with polyclonal activators, such as immobilized or cross-linked anti-CD3 monoclonal antibodies (mAbs) to provide the first signal to T-cells. Other methods take advantage of the secondary T-cell activation pathway to provide the first signal, such as the use of immobilized or cross-linked anti-CD2 mAb.

The combination of anti-CD3 mAb (first signal) and anti-CD28 mAb (second signal) is most commonly used to substitute for natural APCs in inducing T-cell activation in cell therapy protocols. The signals provided by anti-CD3 and anti-CD28 mAbs are best delivered to T-cells when the antibodies are immobilized on a solid surface such as plastic plates (Baroja, Lorre et al. 1989; Damle and Doyle 1989) or sepharose beads (Anderson, Blue et al. 1988) (see also U.S. Pat. No. 6,352,694 issued to June, et al.).

A method for immobilizing anti-CD3 and anti-CD28 mAb on tosyl-activated paramagnetic beads with a 4.5 micron diameter and the subsequent use of these beads to stimulate T-cells to proliferate and produce pro-inflammatory cytokines has been described (Levine, Bernstein et al. 1997). It has also been shown that T-cells activated with these beads exhibit properties, such as cytokine production, that make them potentially useful for adoptive immunotherapy (Garlie, LeFever et al. 1999; Shibuya, Wei et al. 2000). These beads are now commercially available from Dynal, NS (Oslo, Norway) under the trade name Dynabeads® CD3/CD28 T-cell Expansion.

The use of paramagnetic beads with immobilized mAbs for expansion of T-cells in cell therapy protocols requires the separation and removal of the beads from the T-cells prior to patient infusion. This is a very labor-intensive process and results in cell loss, cell damage, increased risk of contamination and increased cost of processing. Because of the tight association of the immobilized mAbs on the beads with the corresponding ligands on the surface of the target T-cells, the removal of the beads from the T-cells is difficult. The bead: cell conjugates are often separated by waiting until the T-cells internalize the target antigens and then by using mechanical disruption techniques to separate the beads from the T-cells. This technique can cause damage to the T-cells and can also cause the ligated antigens on the T-cells to be removed from the cell surface for a period of time (Rubbi, Patel et al. 1993). In addition, highly activated T-cells are most desirable for use in cell therapy protocols and T-cells often lose this desirable property during the 24-72 hour waiting time for the T-cells to internalize the target antigens.

The process of removing the paramagnetic beads after separation from the T-cells requires the passing of the cell/bead solution over a magnet. This process can greatly reduce the quantity of beads remaining with the T-cells, but does not completely eliminate the beads. This incomplete bead removal results in some beads being infused in patients which can cause toxic effects. The magnetic bead removal process also reduces the number of T-cells available for therapy, as many T-cells remain associated with the paramagnetic beads even after the waiting time and mechanical disassociation, and are thus removed with the beads in the magnetic field. Some cell loss also occurs when T-cells that may not be bound to the beads become entrapped by beads pulled to the surface next to the magnetic source.

SUMMARY OF THE INVENTION

The present invention includes a biodegradable device for activating T-cells including a biodegradable support and a binder attached to the biodegradable support, the binder having reactivity to one or more agents capable of binding to a T-cell surface antigen.

The present invention also includes a method for activating T-cells, the method comprising attaching one or more T-cell activators to a population of T-cells and mixing the T-cells with a biodegradable support with an attached binder having reactivity to the T-cell activators.

DETAILED DESCRIPTION OF ILLUSTRATIVE EMBODIMENTS

The present invention utilizes a biodegradable support material coated with a first material capable of immobilizing or cross-linking one or more second materials with reactivity for structures on the surface of a T-cell. The biodegradable nature of the support material eliminates the need to employ a process to separate and remove the support from the T-cells prior to infusion into a patient.

Use of biodegradable materials in medical applications are well known. These materials have been used for encapsulation of proteins for vaccination and controlled drug release (see for example U.S. Pat. No. 6,572,894 issued to Rossling, et al.). Biodegradable materials have also been formulated for use as sutures (see e.g., Bezemer at al., U.S. Pat. No. 6,500,193), and have been used in tissue engineering applications (see e.g., Vert et al. in U.S. Pat. No. 4,279,249 and Slivka, et al in U.S. Pat. No. 6,511,511) and used as implants (see e.g., Leatherbury, et al. in U.S. Pat. No. 6,514,286). The physical and chemical properties of the biodegradable material for use in these prior art applications differ significantly from the requirements of the present invention. Prior art applications require slow, controlled degradation and encapsulation of active ingredients and/or high tensile strength and stability. The application of the present invention requires rapid degradation which does not need to be at a controlled rate and also does not require high tensile strength. Second, materials only need to be cross-linked for a period of 4 to 24 hours in order to deliver a signal to T-cells. In addition, the present invention does not require encapsulation of an active ingredient as in most prior art methods using biodegradable microspheres.

The biodegradable material selected for use in the present invention must be non-toxic and non-antigenic in humans, and preferably must be capable of being delivered to humans parenterally, preferably intravenously. The biodegradable material can be derived from natural or synthetic materials that degrade in biological fluids. It is preferable that degradation occur using non-enzymatic means. For purposes of the present invention, biological fluids include cell culture media and blood. The biodegradable material must degrade rapidly (i.e., within a month, preferably within 2 weeks, more preferably within 1 week, and most preferably within 3 days). The biodegradable material degradation products must produce non-toxic by-products that can be metabolized and/or excreted via normal physiological pathways.

It is also preferable that biodegradable materials used in formulating the device of the present invention do not utilize organic solvents in the manufacturing process, as these solvents pose a health risk on long-term exposure in humans. However, a preferred embodiment is the formulation of microspheres from synthetic polymers of which virtually all fabrication processes require use of an organic solvent such as dichloromethane. If organic solvents are utilized in the manufacture of the biodegradable supports, attempts should be made to reduce the amount of residual solvent in the final formulation. Acceptable residual solvent concentrations are determined by regulatory agencies. For example, ICH (International Conference on Harmonization) guidelines set the maximal permissible dichloromethane levels in the blood at 6 mg/day.

Examples of suitable natural materials for use as biodegradable supports include proteins such as collagen, gelatin and albumen and polysaccharides such as starch, dextran, inulin, cellulose and hyaluronic acid.

Examples of synthetic materials for use as biodegradable supports include aliphatic polyesters, such as poly(lactic acid) (PLA), poly(glycolic acid) (PGA), copolymers of PLA and PGA (PLGA) or poly(carprolactone) (PCL), and polyanhydrides. These materials have been widely used as biodegradable polymers in medical applications. Synthetic polymers in general offer greater advantages over natural materials in that they can be tailored to give a wider range of properties and have more predictable lot-to-lot uniformity.

The factors which affect the physical properties and performance of biodegradable polymers are well known. These factors include monomer selection, initiator selection, process conditions and the presence of additives. These factors in turn influence the polymer's hydrophilicity, crystallinity, melt and glass transition temperatures, molecular weight distribution, end groups, sequence distribution (random vs. blocky) and the presence of residual monomer additives.

In general, for the purposes of the present invention, polymers should be selected for high hydrophilicity, polymers may be either semicrystalline or amorphous, preferably amorphous, with a glass transition temperature that is preferably well above 37° C., allowing the polymer to act more like a glass than a rubber at body temperature. Polymers should have a low molecular weight distribution and low inherent viscosity for accelerated degradation, and the preference is for random over blocky compositions for the same reason.

Biodegradable polymers can be formulated into various shapes, such as films, strips, fibers, gels, meshes, sponges and spheres (such as nanospheres or microspheres). They can also be extruded, injection molded, compression molded, or solvent or spun cast. The primary processing may also be followed by subsequent machining into final parts.

The choice of shape is dependent on the cell therapy application. For example, if the biodegradable material is to be used only to culture T-cells ex-vivo, but will be degraded so as not to be infused into a patient, the formulation of a matrix with high surface area is preferred. Such a matrix would preferably simulate the structure of dendritic cells in the lymph nodes, providing interconnecting star-burst like structures or honey-combed structure shapes.

Microspheres are a preferred formulation because of the simplicity of manufacture and the spherical shape allows an increased surface area for interaction with cellular receptors. Small microsphere particle sizes of 1 to about 500 µm enables direct injection into the body by conventional methods. Thus the spherical shaped device can be used both for the cell culture and infusion steps of a cell therapy protocol. Nanospheres can also be utilized, however, nanospheres do not provide enough cross-linking to activate naïve T-cells and thus can only be used with previously activated T-cells. In preferred embodiments, microspheres that range in size from 1 µm to 10 µm are formulated.

According to the method of the present invention, the biodegradable support is first formulated into a shape, such as a microsphere. The biodegradable support is then coated with a first material providing a reactive surface which is capable of binding to one or more second materials. The second materials have a reactive surface which permits binding to surface structures on a cell. In preferred embodiments, second materials are capable of transducing a signal to a cell through interaction with a surface expressed cellular receptor.

In practice of the invention, the second materials can be first bound to the first material on the biodegradable support and then mixed with the target T-cells, whereby the second materials bind to surface structures on the T-cells. Alternatively, the second materials can be first bound to the surface structures of the T-cells and the T-cells with the bound second material then mixed with the biodegradable support coated with the first material. In both cases, the final mixture contains a biodegradable support coated with a first material, such first material which is bound to one or more second materials, and such second materials which are bound to surface structures on a T-cell.

The first material can be attached to the biodegradable support by means of absorption, reactive groups, or by means of a coupling agent or linker. The terms "coupling agent" or "linker" as used herein refer to bifunctional crosslinking or coupling agents such as molecules containing two reactive groups which may be separated by a spacer.

Suitable first materials are any biocompatible material capable of binding to a portion of the second material. Examples of suitable first materials include polyclonal or monoclonal antibodies, or fragments thereof, and bioactive substances such as Protein A, avidin or biotin. In embodiments where the second materials are mouse-derived proteins, such as mouse antibodies, suitable first materials are polyclonal antibodies with specificity for the mouse immunoglobulins, such as sheep or goat-derived anti-mouse polyclonal antibodies or anti-mouse monoclonal antibodies such as rat-derived anti-mouse Fc antibodies. In embodiments where the second material is coated with biotin, a suitable first material is avidin or an antibody specific for biotin. Alternatively, where the second material is coated with avidin, a suitable first material is biotin or an anti-avidin antibody. In addition, when the second materials are IgG molecules, the first materials can be agents with high affinity for IgG, such as Protein G or Protein A.

First materials can be chemically coupled to the biodegradable support with glutaraldehyde or other di-aldehyde with or without the first attachment of diaminoheptane spacer groups to the biodegradable support. Covalent bonding by nucleophilic displacement to biodegradable supports activated with tosyl groups (p-toluenesulfonyl), through cyanogens bromide activation or other similar methods can also be used. The biodegradable support could also be coated directly with avidin or biotin to interact with a second material such as a mitogenic protein coated with the opposite corresponding biotin or avidin.

Suitable second materials are biocompatible materials which are capable of binding to a cell surface structure. Preferably, the binding of the second material to the T-cell surface will transduce a signal to the T-cell when the second agent is immobilized or cross-linked by the first material. Signal transduction will have the effect of causing the target T-cell to perform a function desirable in cell therapy applications, such as proliferate, produce cytokines, differentiate and/or express effector molecules such as FasL, TRAIL and CD40L.

Examples of suitable second materials for use in the present invention include agents such as synthesized compounds, nucleic acids and proteins, including polyclonal or monoclonal antibodies, and fragments or derivatives thereof, and bioengineered proteins, such as fusion proteins. In one example, the second materials are mitogenic proteins. Mitogenic proteins are two or more proteins that are able to deliver the requisite minimum of two signals to T-cells in order to cause the T-cells to become activated. Examples of mitogenic proteins are anti-CD3 and anti-CD2 mAbs, in combination with a co-stimulatory protein such as and including proteins specific for one or more of the following T-cell surface molecules: CD28, CD5, CD4, CD8, MHCI, MHCII, CTLA-4, ICOS, PD-1, OX40, CD27L (CD70), 4-1BBL, CD30L and LIGHT, including the corresponding ligands to these surface structures, or fragments thereof.

Other suitable second materials include agents capable of delivering a signal to T-cells through cytokine receptors such as IL-2R, IL-12R, IL-1R, IL-15R; IFN-gammaR, TNF-alphaR, IL-4R, and IL-10R, including mAbs to these receptors, fusion proteins with a reactive end specific for these receptors and the corresponding ligands to these receptors or fractions thereof. Other suitable second materials include any agent capable of binding to cellular adhesion molecules on T-cells such as mAbs, fusion proteins and the corresponding ligands or fractions thereof to adhesion molecules in the following categories: cadherins, ICAM, integrins, and selectins. Examples of adhesion molecules on T-cells are: CD44, CD31, CD18/CD11a (LFA-1), CD29, CD54 (ICAM-1), CD62L (L-selectin), and CD29/CD49d (VLA-4). Other suitable second materials include any agents capable of binding to chemokine receptors, including those in the C-C and C-X-C categories. Examples of chemokine receptors associated with T-cell function include CCR1, CCR2, CCR3, CCR4, CCR5, and CXCR3.

In one embodiment of the present invention, the biodegradable support material is constructed from a linear polyester polymer containing a mixture of lactic acid and glycolic acid. This class of polymers meets the requirements of biocompatibility and biodegradation into harmless end products. These polymers, hereinafter referred to as PLGA, are degraded by ester hydrolysis into lactic acid and glycolic acid. PLGA has been shown to possess excellent biocompatibility. The innocuous nature of PLGA can be exemplified by the approval by the regulatory authorities, including the U.S. Food and Drug Administration, of several parenteral delayed release preparations based on these polymers. Parenterally administrable delayed release products currently on the market and based on PLGA include Decapepty™ (Ibsen Biotech), Prostap S®. (Lederle), Decapeptyl®, Depot (Ferring) and Zoladex® (Zeneca).

Copolymers of DL-lactate and glycolide, rather than L-lactate and glycolide, are preferred because they are amorphous when DL-lactate is a major component, as opposed to semi-crystalline when L-lactate is a major component. This property decreases the degradation time of the polymer. The inherent viscosity (abbreviated as "I.V."; units are in deciliters/gram) of the polymer is a measure of its molecular weight. Preferably, the inherent viscosity of the polymer is from about 0.10 dL/g to about 1.0 dL/g (as measured in chloroform), more preferably from about 0.10 dL/g to about 0.50 dL/g and most preferably from 0.10 to 0.30 dL/g.

Suitable biodegradable polymer material is a 50/50 mixture of poly(DL-lactide co-glycolide). The polymer can be purchased from commercial suppliers such as Birmingham Polymers, Inc (Birmingham, Ala.) under the trade name Lactel®. The 50/50 DL-PLG product number 50DG020 with a inherent viscosity of 0.15 to 0.25 dl/g is a preferred material for use in the present invention. Another preferred material is 50/50 DL-PLG with an inherent viscosity of 0.32 to 0.44 dl/g manufactured by Boehringer Ingelheim (Ingelheim, Germany) under the trade name Resomer® RG 503. Another preferred material is Lactel® 50/50 DL-PLG product number 50D040 (Birmingham Polymers) with a 0.26 to 0.54 inherent viscosity. In other preferred embodiments, polymer end groups can be added to the biodegradable polymers, such as monofunctional alcohol, water or alpha-hydroxy acid, or PEG in order to increase the hydrophilicity of the polymer and thus increase the degradation time and provide active groups for covalent binding of first materials to the polymer.

In a preferred embodiment, the 50/50 DL-PLG is formulated into microspheres.

Microspheres can be prepared by various known methods, including solvent evaporation, phase separation, spray-drying, or solvent extraction at low temperature. The process selected should be simple, reproducible and scalable. The resulting microspheres should be free-flowing and not aggregates in order to produce a uniform syringeable suspension.

The microspheres must also be sterile. This can be ensured by a terminal sterilization step and/or through aseptic processing.

In a preferred embodiment, the solvent evaporation method is utilized to produce the microspheres (McGinity and O'Donnell 1997). To produce microspheres with this method, the hydrophobic 50/50 DL-PLG polymer is dissolved in a water-immiscible organic solvent to give a polymer solution. The solution is then added into an aqueous solution of a surfactant to form an emulsion system and stirred. The faster the stirring speed, the smaller the size of the microspheres. Microspheres are obtained by subsequently evaporating the solvent by continuous stirring, which can be under vacuum or heat.

The water-miscible organic solvents of the present invention need to be non-toxic to the body. Typical examples of organic solvents are members selected from the group consisting of acetic acid, lactic acid, formic acid, acetone, acetonitrile, dimethyl formamide, dimethyl acetamide, dimethyl sulfoxide, dioxane, and N-methyl pyrrolidone and mixtures thereof. Preferably, the water-miscible organic solvent is a member selected from the group consisting of acetic acid, lactic acid, N-methyl pyrrolidone, or a mixture thereof. The water-miscible organic solvent may be used alone or in a mixture with water.

The aqueous phase can contain an emulsion stabilizer that is preferably soluble in water and alcohol, is capable of increasing viscosity of the suspending medium (water-miscible alcohol) when dissolved in the medium, is non-toxic to the body and causes no environmental problems. Typical examples of emulsion stabilizer solutions are: water-soluble synthetic polymers such as polyvinylpyrrolidone, poly(ethylene glycol), and poloxamer; cellulose derivatives such as hydroxypropyl cellulose and hydroxypropylmethyl cellulose, and preferably, polyvinylpyrrolidone and hydroxypropyl cellulose. The content of emulsion stabilizer in the water-miscible alcohol is preferably within the range of 0.1 to about 50% (w/v), and more preferably within the range of 0.2 to about 20% (w/v). The content of emulsion stabilizer can be varied according to the viscosity of the water-miscible alcohol needed.

According to the present invention, the water-miscible alcohol, wherein the emulsion stabilizer is dissolved, is stirred at a temperature of 10 about 80° C., preferably from 20 to about 60° C., and most preferably at room temperature at a speed of 200 to about 20,000 rpm, preferably at a speed of 800 to 1000 rpm. The polymer solution is slowly added to the water-miscible alcohol wherein the emulsion stabilizer is dissolved, and the mixture is stirred from 5 minutes to about 60 minutes. Stirring can be continued for up to 5 hours to allow evaporation of the organic solvent. The resulting microspheres can then collected by centrifugation and washed extensively. The washed microspheres are then ready for attachment of the first material.

The diameter of the microspheres prepared should preferably be within the range from 0.01 to 300 um, and more preferably within the range from 0.1 to 100 um. and most preferably between 1 and 10 um. The particle size (diameter of the microspheres) can be controlled by adjusting the stirring speed during processing, the viscosity of the water-miscible alcohol, and the viscosity of the polymer solution.

Post-coating of the biodegradable support with the first material can be accomplished by a variety of standard methods depending upon the nature of the first material. For most applications where the first material is a protein, passive absorption techniques are adequate for protein attachment to the biodegradable support. Other applications may require direct covalent attachment or covalent attachment through a linking group, such as when using first materials with low affinity for the biodegradable support, or use of first materials such as DNA, lectins, enzymes and drugs, or in applications where the biodegradable device is used in an environment where a material is used that will displace the passively absorbed first material. Various schemes of modification to the surface of the biodegradable support can be used to introduce applicable functional groups for covalent protein immobilization including: hydrolysis to form carboxylic groups (the immobilization is carried out through the protein's amino groups using condensing agents), hydrazinolysis to form hydrazide groups (immobilization through the aldehyde groups of the glycoprotein's carbohydrate fragments oxidized with periodate), aminolysis with bifunctional amines (condensation with the protein's carboxylic groups), modification with glutaric aldehyde (immobilization through the amino and sulfhydryl groups of a protein) (Ertl, B., F. Heigl, et al. (2000). "Lectin-mediated bioadhesion: preparation, stability and caco-2 binding of wheat germ agglutinin-functionalized Poly(D,L-lactic-co-glycolic acid)-microspheres." *J Drug Target* 8(3): 173-84. Muller, M., J. Voros, et al. (2003). "Surface modification of PLGA microspheres." *J Biomed Mater Res* 66A(1): 55-61. Tessmar, J., A. Mikos, et al. (2003). "The use of poly(ethylene glycol)-block-poly(lactic acid) derived copolymers for the rapid creation of biomimetic surfaces." *Biomaterials* 24(24): 4475-86.). Proteins are known to satisfactorily retain their stability on such matrices.

After coating a first material to the surface of the biodegradable support directly or through a linker, it is desirable to block non-specific adsorption of proteins that may be present during cell culture or upon infusion to a patient. Any innocuous protein may be used for this purpose. Bovine or human serum albumin are desired blocking agents. In cases where the large size of the albumin obscures the activity of smaller active first material proteins, glycine or small polypeptides can be used as alternative blocking agents.

If the biodegradable supports are formulated into particles of less than 0.5 μm, the chemical aspects of the attachment to the biodegradable support will remain the same, but the mechanical aspects have to be adapted. Most protocols will utilize centrifugation to separate particles from reagents used in the first agent attachment process. However, this is not practical for particles of sizes of less than about 0.5 μm since most microcentrifuges cannot spin this size particles down within 30 minutes and extremely high G-forces are not recommended as it becomes very arduous to resuspend the particles. In this situation, alternative separation techniques are indicated, such as dialysis or forced membrane filtration. Commercial kits that use hollow fiber filtration techniques are also available for effective separation of 0.1-0.5 μm. particles.

In one embodiments, first materials that are proteins can be bond to the biological support material by adsorption with standard known methods. One method for adsorbing a protein to the biodegradable support where the support is formulated into microspheres is to suspend the microspheres in 0.1M Borate buffer at pH 8.5, spin down and resuspend the microspheres 2 or 3 times. The first material protein is then suspended in the borate buffer and added to the microspheres. The mixture is mixed end-to-end for at least 4 hours and for up to 24 hours. The mixing is preferably conducted at 4° C. After mixing, the microspheres are spun and the supernatant removed and analyzed for protein determination. The coated microspheres are then resuspended in a physiological buffer, such as phosphate buffered saline containing a blocking agent, such as 1-5% bovine serum albumen and/or 0.05% w/v Tween 20.

The coated biodegradable supports can then be combined with the desired second materials or the second materials can be bound to the target T-cells and then mixed with the first material-coated biodegradable supports.

During processing, it is necessary to minimize the presence of moisture to avoid excessive degradation of the biodegradable support by hydrolysis prior to use. To avoid hydrolytic degradation, extra precautions during processing are necessary. Steps should be taken to dry the biodegradable polymers during processing. Polymers can be dried by incubating the polymer at 80° C. for 24 h. Drying can also be accomplished by vacuum drying or drying in a recirculating air dryer. Care must be taken when drying polymers above room temperature, as some amorphous compositions may fuse when the drying temperature exceeds the glass transition temperature.

The biodegradable devices are best packaged in small aliquots so that the material is used quickly once the package is opened. Packaging should be in desiccated moisture proof bags. The devices can be sterilized by a variety of methods such as storage in alcohol, gamma radiation or ethylene oxide gas. Biodegradable devices should not be sterilized by autoclave as the high temperatures can cause degradation.

The devices of the present invention can also be stored by flash freezing and then stored in liquid nitrogen and can also be lyophilized prior to storage.

EXAMPLES

The following examples are included for illustrative purposes only and are not intended to limit the scope of the invention.

Example #1

Microsphere Preparation

The solvent evaporation method was used for preparation of microspheres. Lactel® (Birmingham Polymers, Birmingham, Ala.) 50/50 DL-PLG product number 50DG020 with a inherent viscosity of 0.15 to 0.25 dl/g was used as the polymer. The DL-PLG powder was dissolved in 20 ml of methylene chloride to a final 5% DL-PLG w/v ratio. The 5% DL-PLG solution was then added dropwise to 125 ml of 2.4% hydroxypropylmethylcellulose in 0.1M glycine/HCl buffer pH 1.1 under constant stirring at 1000 rpm at room temperature (25±2° C.). Stirring was maintained until complete evaporation of the organic solvent (about 3 hours). Microspheres were collected by centrifugation at 1000 rpm, 5 min at 4° C. followed by three cycles of washing with distilled water, filtered and dried overnight. The microsphere sizes ranged from 3.0 to 7.0 um with a CV maximum of ≦10%.

Coating with First Material

Polyclonal goat anti-mouse polyclonal antibody was suspended in 30 ml of PBS solution with 5% human serum albumen (HSA) at a concentration of 10 ug/ml. This solution was used to resuspend the dried microspheres at a concentration of approximately $2 \times 10^8$ particles per ml. The microspheres and the polyclonal antibody were mixed end over end at 4° C. for 8 hours. The microspheres were then washed 3 times in PBS with HSA, filtered and dried.

Application of Second Material

For one group of experiments, second materials were added directly to the goat anti-mouse antibody coated microspheres. For this purpose, a 50/50 mixture of anti-human CD3 mAb and anti-human CD28 mAbs at a final concentration of 10 ug/ml were prepared in PBS containing 5% HSA. This solution was then used to resuspend the coated microspheres at a final concentration of $2 \times 10^8$ particles per ml. The mixture was vigorously mixed end to end for 4 hours at room temperature, washed 3 times, filtered and dried overnight.

Results

Microsphere Size

In order to determine the size distribution of the microspheres, a liquot of the spheres was analyzed by laser diffraction (Shimadzu Laser Diffraction Type Particle Analyzer) and by phase contrast microscopy. For laser diffraction studies, the microspheres were suspended in PBS containing 0.2% Tween as a wetting agent. The mixture was sonicated for 1 min and analyzed under stirred conditions to minimize aggregate formation. The distribution (after eliminating aggregates) indicated spheres ranging in size from 4 to 24 microns with a mean of 7 microns.

Binding of First Material

In order to verify the coating of the first material, microspheres absorption coated with goat anti-mouse polyclonal antibody was suspended in PBS containing 1% HSA and stained with a FITC-conjugated mouse IgG mAb. As a control, non-coated microspheres were stained under the same conditions. The beads were then analyzed by flow cytometry. The coated beads showed intense staining indicating successful coating with the first material.

Example #2

Biological Effect of Second Materials

To determine the effect on proinflammatory cytokine production of T-cells stimulated with the method of the invention compared to prior art stimulation methods, the following study was conducted:

PBL were isolated by Percoll gradient centrifugation from leukopacks obtained by apheresis of healthy donors. CD4+ T-cells were purified by positive selection using anti-CD4 microbeads (Miltenyi Biotech, Germany). Cells were cultured in X-Vivo 15 (BioWhittiker) supplemented with glutamine. Purified CD4+ cells were placed in 24 well plates and were incubated with either goat anti-mouse coated microspheres coated directly with anti-CD3 and anti-CD28 mAbs in a 50:50 ratio (direct method) or the cells were first labeled with the anti-CD3 and anti-CD28 mAbs and then incubated with the coated microspheres. As a negative control, unlabelled cells were incubated with polyclonal goat anti-mouse coated microspheres. As a positive control, cells were incubated with CD3/CD28 coated Dynabeads. All groups were adjusted to a bead:cell ratio of 3:1.

Purified CD4+ cells were placed in the wells at cell densities of $0.5 \times 10^6$ per ml. Concentrations of cytokines in the cell-free supernatants after 72 hours was measured by ELISA.

The cytokine data represents the mean+/−SD of six different blood samples.

| Method | IFN-gamma (pg/ml) | TNF-alpha (pg/ml) |
|---|---|---|
| Microspheres direct | 1019 +/− 36 | 695 +/− 98 |
| Microspheres indirect | 5859 +/− 29 | 4988 +/− 122 |
| Dynabeads control | 1349 +/− 48 | 654 +/− 101 |
| Negative control | N.D. | N.D. |

These data show that the indirect method of the present invention enhances the Th1 cytokine production from primary T-cells.

Example #3

Proliferation

CD4+ cells were prepared as described in the example above except that the cultures were continued for 9 days. Fresh beads and/or antibodies were added every three days when the cultures were split to a concentration of $0.5\text{-}1\times10^6$ cells/ml. Cells were seeded in triplicate at the beginning of each experiment.

| Method | Starting cell # (in $10^6$ cells) | Ending cell # (in $10^6$ cells) |
| --- | --- | --- |
| Microspheres direct | 1 | 25 |
| Microspheres indirect | 1 | 58 |
| Dynabeads control | 1 | 22 |
| Negative control | N.D. | N.D. |

Although the present invention has been described with reference to preferred embodiments, workers skilled in the art will recognize that changes may be made in form and detail without departing from the spirit and scope of the invention.

The invention claimed is:

1. A method for activating T-cells comprising:
   attaching more than one second material to a population of T-cells; and
   mixing the T-cells with a support with an attached first material, wherein the first material is capable of cross-linking the more than one second material.

2. The method of claim 1 wherein the first material comprises polyclonal or monoclonal antibodies, or fragments thereof, protein A, avidin or biotin.

3. The method of claim 1 wherein the first material is attached to the support with glutaraldehyde.

4. The method of claim 1 wherein the first material is initially attached to the support prior to mixing with the T-cells.

5. The method of claim 4 and further applying a blocking agent to the first material after attachment to the support, the blocking agent to be used for blocking non-specific absorption of proteins.

6. The method of claim 1 wherein the second materials comprise mitogenic proteins, monoclonal antibodies, fusion proteins, materials capable of binding to chemokine receptors or combinations thereof.

7. The method of claim 6 wherein the mitogenic proteins include anti-CD3 and anti-CD2 monoclonal antibodies.

8. The method of claim 1 wherein the support is a biodegradable support.

9. The method of claim 8 wherein the biodegradable support is made of a biodegradable material formed into a substantially spherically configuration.

* * * * *

UNITED STATES PATENT AND TRADEMARK OFFICE
CERTIFICATE OF CORRECTION

| | |
|---|---|
| PATENT NO. | : 8,012,750 B2 |
| APPLICATION NO. | : 12/533668 |
| DATED | : September 6, 2011 |
| INVENTOR(S) | : Michael Har-Noy |

It is certified that error appears in the above-identified patent and that said Letters Patent is hereby corrected as shown below:

<u>Title page,</u>
Item 54, please correct the title with --METHOD FOR ACTIVATING T-CELLS--

Signed and Sealed this
Second Day of October, 2012

David J. Kappos
*Director of the United States Patent and Trademark Office*

UNITED STATES PATENT AND TRADEMARK OFFICE
CERTIFICATE OF CORRECTION

PATENT NO. : 8,012,750 B2  
APPLICATION NO. : 12/533668  
DATED : September 6, 2011  
INVENTOR(S) : Michael Har-Noy Page 1 of 1

It is certified that error appears in the above-identified patent and that said Letters Patent is hereby corrected as shown below:

Title page, Item (54) and at Column 1, line 1,
Please correct the title with --METHOD FOR ACTIVATING T-CELLS--

This certificate supersedes the Certificate of Correction issued October 2, 2012.

Signed and Sealed this
Sixth Day of November, 2012

David J. Kappos
*Director of the United States Patent and Trademark Office*